United States Patent
Reiderman

(10) Patent No.: US 8,294,468 B2
(45) Date of Patent: Oct. 23, 2012

(54) METHOD AND APPARATUS FOR WELL-BORE PROXIMITY MEASUREMENT WHILE DRILLING

(75) Inventor: Arcady Reiderman, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 580 days.

(21) Appl. No.: 11/848,333

(22) Filed: Aug. 31, 2007

(65) Prior Publication Data

US 2008/0018334 A1 Jan. 24, 2008

Related U.S. Application Data

(63) Continuation-in-part of application No. 11/037,488, filed on Jan. 18, 2005.

(51) Int. Cl.
*G01V 3/00* (2006.01)
(52) U.S. Cl. ............. 324/346; 324/338; 175/45; 702/9
(58) Field of Classification Search .............. 324/372, 324/346; 175/45
See application file for complete search history.

(56) References Cited

U.S. PATENT DOCUMENTS

| | | | |
|---|---|---|---|
| 3,453,530 A | 7/1969 | Attali | |
| 3,731,752 A | 5/1973 | Schad | 175/45 |
| 4,205,288 A | 5/1980 | Lin et al. | |
| 4,323,848 A | 4/1982 | Kuckes | 324/338 |
| 4,372,398 A | 2/1983 | Kuckes | 175/45 |
| 4,409,846 A | 10/1983 | Ueno | |
| 4,443,762 A | 4/1984 | Kuckes | 324/346 |
| 4,465,140 A | 8/1984 | Hoehn, Jr. | |
| 4,529,939 A | 7/1985 | Kuckes | 324/346 |
| 4,700,142 A | 10/1987 | Kuckes | 324/346 |
| 4,736,634 A | 4/1988 | Amata | |
| 4,791,373 A | 12/1988 | Kuckes | 324/346 |
| 4,845,434 A | 7/1989 | Kuckes et al. | 324/346 |
| 4,933,640 A * | 6/1990 | Kuckes | 324/346 |
| 5,074,365 A | 12/1991 | Kuckes | 175/40 |
| 5,084,678 A * | 1/1992 | Hutin | 324/346 |
| 5,086,554 A | 2/1992 | Murata et al. | |
| 5,218,301 A | 6/1993 | Kuckes | 324/346 |
| 5,305,212 A | 4/1994 | Kuckes | 364/422 |
| 5,343,152 A | 8/1994 | Kuckes | 324/346 |
| 5,485,089 A | 1/1996 | Kuckes | 324/346 |
| 5,512,830 A | 4/1996 | Kuckes | 324/346 |
| 5,513,710 A | 5/1996 | Kuckes | 175/45 |
| 5,515,931 A | 5/1996 | Kuckes | 175/45 |
| 5,582,248 A * | 12/1996 | Estes | 166/255.2 |
| 5,589,775 A * | 12/1996 | Kuckes | 324/346 |
| 5,657,826 A | 8/1997 | Kuckes | 175/45 |
| 5,675,488 A | 10/1997 | McElhinney | 364/422 |
| 5,725,059 A | 3/1998 | Kuckes et al. | 175/45 |
| 5,923,170 A | 7/1999 | Kuckes | 324/326 |
| 6,791,331 B2 | 9/2004 | Conti | |
| 6,927,577 B2 * | 8/2005 | Nelson | 324/329 |
| 6,937,023 B2 | 8/2005 | McElhinney | 324/347 |
| 6,985,814 B2 | 1/2006 | McElhinney | 702/7 |
| 7,046,009 B2 | 5/2006 | Itskovich | |
| 7,568,532 B2 * | 8/2009 | Kuckes et al. | 175/40 |
| 2003/0076107 A1 | 4/2003 | Fanini et al. | |
| 2003/0129763 A1 | 7/2003 | Chamberlain et al. | |
| 2004/0183538 A1 | 9/2004 | Hanstein et al. | 324/339 |
| 2005/0030021 A1 | 2/2005 | Prammer et al. | |
| 2005/0189945 A1* | 9/2005 | Reiderman | 324/333 |
| 2005/0247484 A1* | 11/2005 | Brune et al. | 175/45 |

* cited by examiner

*Primary Examiner* — Jay Patidar
*Assistant Examiner* — David M. Schindler
(74) *Attorney, Agent, or Firm* — Mossman Kumar & Tyler PC

(57) ABSTRACT

A rotating, transversely magnetized, magnet on a drill collar induces magnetization in a casing of a preexisting well. A coil rotating synchronously with the magnet produces a current at twice the frequency of rotation and having an amplitude that depends upon the distance from the magnet to the preexisting well. Alternatively, a variable magnetic field is produced in the casing using a switchable magnet.

24 Claims, 6 Drawing Sheets

METHOD AND APPARATUS FOR WELL-BORE PROXIMITY MEASUREMENT WHILE DRILLING

CROSS-REFERENCE TO RELATED APPLICATION

This application is a continuation-in-part of U.S. patent application Ser. No. 11/037,488 filed on Jan. 18, 2005.

BACKGROUND OF THE DISCLOSURE

1. Field of the Disclosure

This disclosure relates generally to methods for performing measurement while drilling applications. More particularly, this disclosure relates to a new and improved apparatus and method for determining a distance to a pre-existing wellbore and controlling drilling operations based on the determination.

2. Background of the Art

In the process of drilling wells for hydrocarbon production, it is commonly necessary to drill a second well in a predetermined relationship to an existing well. An example of this may be when a blowout occurred in the existing well; two approaches may be taken to control the blowout. One method is to use explosives at the surface and snuff out the fire in the burning well. This procedure is fraught with danger and requires prompt control of hydrocarbons flow in the well. The second method is to drill a second borehole to intersect the blowout well and pump drilling mud into the blowout well. This is not a trivial matter. An error of half a degree can result in a deviation of close to 90 feet at a depth of 10,000 feet. A typical borehole is about 12 inches in diameter, a miniscule target compared to the potential error zone.

Another situation in which accurate drilling is required is in secondary recovery operations. For various reasons, such as low formation pressure or high viscosity of hydrocarbons in the reservoir, production under natural conditions of hydrocarbons may be at uneconomically low rates. In such cases, a second borehole is drilled to be substantially parallel to the pre-existing borehole. Fluid such as water, $CO_2$ is then injected into the formation from the second borehole and the injected fluid drives the hydrocarbons in the formation towards the producing borehole where it may be recovered.

In 1970, Shell Oil Co.'s Cox 1, a 22,000-ft Smackover exploratory well, blew out near Piney Woods, Miss. This challenge led to the first direct intersection of a blowout tubular using an acoustic detection method. Wireline instruments were developed to detect proximity of a tubular by measuring distance and direction from the relief well to the blowout casing using the noise from the flowing gas in the blowout well. More recently, electromagnetic methods have been used to determine the distance to the cased preexisting well.

The electromagnetic techniques fall into 2 categories. In the first category, referred to as active ranging, a source of AC magnetic field and a magnetic sensor are placed in different wells. The source can be a solenoid placed in the production well or an electric current injected in the production well casing. The magnetic field produced by the current in the casing is measured in the drilling well. The active ranging approach can probably offer a good accuracy of measurements, but suffers from the drawback that access to the pre-existing well is required.

In the second category are passive ranging techniques that do not require access to the pre-existing well while drilling the second well. The techniques normally utilize a relatively strong magnetism induced in the casing of the pre-existing well by the Earth's magnetic field. The signal due directly to the earth's magnetic field is a problem, limiting the accuracy of this measurement. Residual magnetism of the casing introduces additional uncertainties. The following US patents reflect some of the techniques proposed and used for magnetic ranging: U.S. Pat. No. 4,323,848 to Kuckes; U.S. Pat. No. 4,372,398 to Kuckes; U.S. Pat. No. 4,443,762 to Kuckes; U.S. Pat. No. 4,529,939 to Kuckes; U.S. Pat. No. 4,700,142 to Kuckes; U.S. Pat. No. 4,791,373 to Kuckes; U.S. Pat. No. 4,845,434 to Kuckes; U.S. Pat. No. 5,074,365 to Kuckes; U.S. Pat. No. 5,218,301 to Kuckes; U.S. Pat. No. 5,305,212 to Kuckes; U.S. Pat. No. 5,343,152 to Kuckes; U.S. Pat. No. 5,485,089 to Kuckes; U.S. Pat. No. 5,512,830 to Kuckes; U.S. Pat. No. 5,513,710 to Kuckes; U.S. Pat. No. 5,515,931 to Kuckes; U.S. Pat. No. 5,675,488 to McElhinney; U.S. Pat. No. 5,725,059 to Kuckes et al.; U.S. Pat. No. 5,923,170 to Kuckes; U.S. Pat. No. 5,657,826 to Kuckes; U.S. Pat. No. 6,937,023 to McElhinney; and U.S. Pat. No. 6,985,814 to McElhinney.

The present disclosure teaches a method in which access to the pre-existing well is not required and the effects of the direct earth's magnetic field are minimized.

SUMMARY OF THE DISCLOSURE

One embodiment of the disclosure is a method of determining a distance to a first borehole from a second borehole. A time varying magnetic field is produced in the first borehole using a magnet in the second borehole. Magnetization in a magnetic object in the first borehole is produced. A coil in the second borehole is used to produce a signal responsive to a magnetic flux resulting from the magnetization. This signal is used to estimate the distance. The magnetic object in the first borehole may be a casing. The method may further include using the estimated distance to maintain a trajectory of the second borehole in a desired relation to the first borehole. The desired relation may be substantially parallel or intersecting. The method may include conveying a magnet on a bottom-hole assembly on a drilling tubular into the second borehole. Producing a time varying field may be done rotating a magnet having a substantially transverse magnetization in the second borehole at a first rotational speed, and producing the signal may be done by rotating the coil synchronously with the magnet. Estimating the distance may further include filtering of the signal to remove an effect of a magnetic field of the earth. The method may further include measuring the first rotational speed, determining a second harmonic component of the first rotational speed, and using the determined second harmonic component to correct the signal. The method may further include measuring an additional signal using a split coil responsive to the magnetic flux, and using the additional signal as an indicator of an inclination between an axis of the first borehole and an axis of the second borehole. The first rotational speed may be substantially the same as a rotational speed of a bottomhole assembly. The time varying field may be produced by switching a polarity of a magnet having a substantially longitudinal magnetization in the second borehole, and producing the signal may be done using a coil with an axis that is substantially longitudinal.

Another embodiment of the disclosure is an apparatus for determining a distance in a first borehole from a second borehole. The apparatus includes a magnet configured to be conveyed in a second borehole and produce a time varying magnetic field and induce a magnetization in a magnetic object in the first borehole. A coil in the second borehole is configured to produce a signal responsive to a magnetic flux resulting from the magnetization. A processor is configured estimate the distance using the signal. The magnetic object in the first borehole may be a casing. The processor may be further configured to use the estimated distance to maintain a trajectory of the second borehole in a desired relation to a trajectory of the first borehole. The desired relation may be substantially parallel and/or intersecting. The apparatus may further include a bottomhole assembly on a drilling tubular configured to convey the magnet into the second borehole. The magnet may be rotating magnet having a substantially transverse magnetization configured to rotate at a first rotational speed, and the coil is configured to rotate synchronously with the magnet. The processor may be further configured to determine the distance by further filtering the signal to remove an effect of a magnetic field of the earth. The apparatus may further include an accelerometer configured to measure the first rotational speed, and the processor may be further configured to determine a second harmonic component of the first rotational speed and use the determined second harmonic component to correct the signal. The apparatus may further include a split coil responsive to the magnetic flux configured to produce an additional signal and the processor may be further configured to use the additional signal as an indicator of an inclination between an axis of the first borehole and an axis of the second borehole. The first rotational speed may be substantially the same as a rotational speed of a bottomhole assembly. The apparatus may include a switchable magnet having a substantially longitudinal magnetization in the second borehole configured to be switched and produce the time varying field, and a coil with an axis that is substantially longitudinal configured to produce the signal. The processor may be further configured to estimate the distance using a portion of the signal substantially excluding a component of the signal due to a direct coupling of the magnet and coil, and substantially excluding a component of the signal due to eddy currents in the formation and a conductive body in the second borehole.

Another embodiment of the disclosure is a computer-readable medium for use with an apparatus for determining a distance to a first borehole from a second borehole. The apparatus includes a magnet configured to be conveyed in a second borehole, produce a time varying magnetic field in the first borehole, and induce a magnetization in a magnetic object in the first borehole. The apparatus also includes a coil in the second borehole configured to produce a signal responding to a magnetic flux resulting from the magnetization. The medium includes instructions which enable a processor to estimate the distance using the signal. The medium may include a ROM, an EPROM, an EEPROM, a flash memory, and/or an optical disk.

BRIEF DESCRIPTION OF THE FIGURES

For detailed understanding of the present disclosure, references should be made to the following detailed description of the preferred embodiment, taken in conjunction with the accompanying drawings, in which like elements have been given like numerals and wherein.

DETAILED DESCRIPTION OF THE DISCLOSURE

Figure 1:
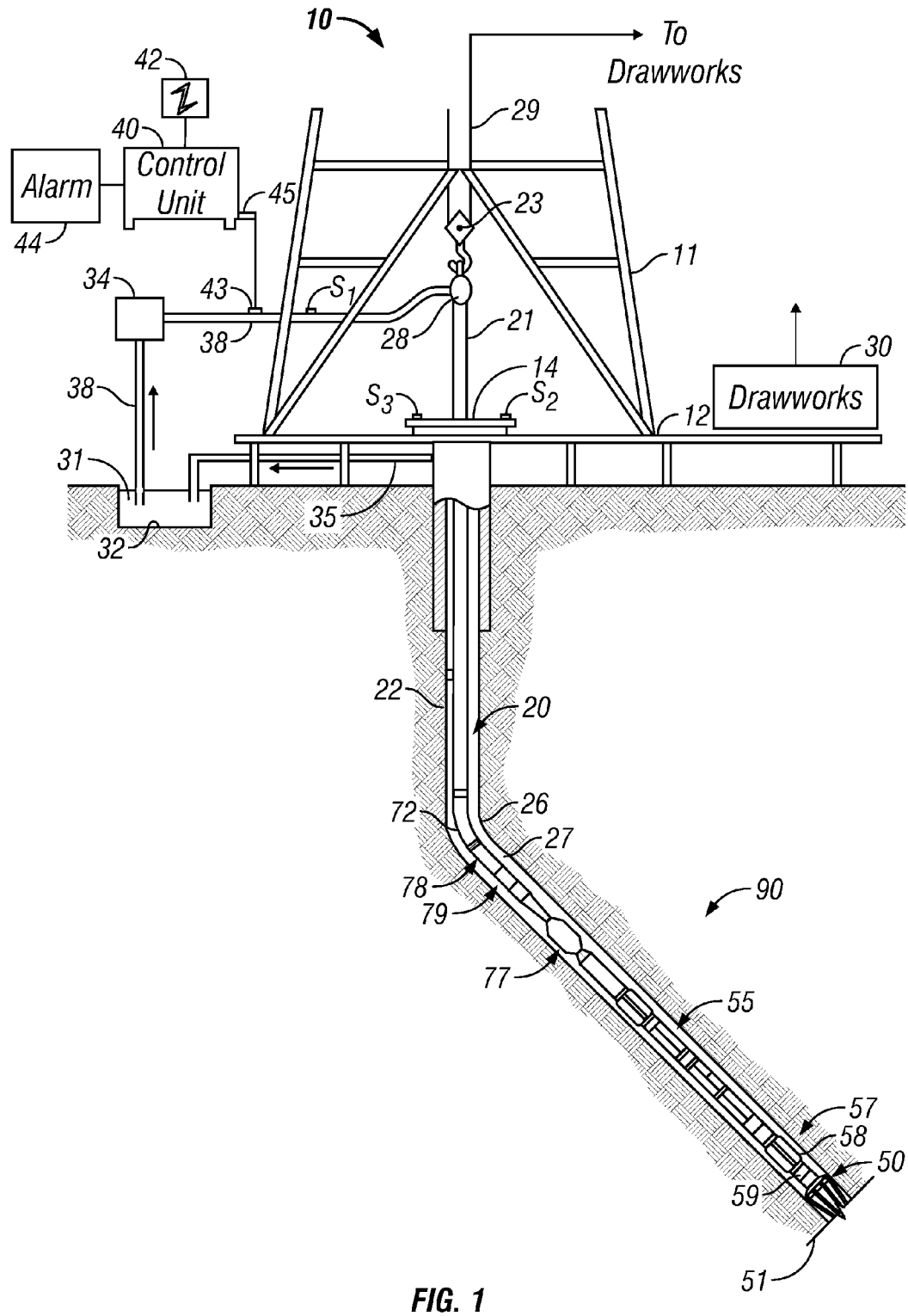
FIG. 1 is a schematic illustration of a drilling system suitable for use with the present disclosure.

FIG. 1 shows a schematic diagram of a drilling system 10 with a drillstring 20 carrying a drilling assembly 90 (also referred to as the bottom hole assembly, or "BHA") conveyed in a "wellbore" or "borehole" 26 for drilling the wellbore. The drilling system 10 includes a conventional derrick 11 erected on a floor 12 which supports a rotary table 14 that is rotated by a prime mover such as an electric motor (not shown) at a desired rotational speed. The drillstring 20 includes a tubing such as a drill pipe 22 or a coiled-tubing extending downward from the surface into the borehole 26. The drillstring 20 is pushed into the wellbore 26 when a drill pipe 22 is used as the tubing. For coiled-tubing applications, a tubing injector, such as an injector (not shown), however, is used to move the tubing from a source thereof, such as a reel (not shown), to the wellbore 26. The drill bit 50 attached to the end of the drillstring breaks up the geological formations when it is rotated to drill the borehole 26. If a drill pipe 22 is used, the drillstring 20 is coupled to a drawworks 30 via a Kelly joint 21, swivel, 28 and line 29 through a pulley 23. During drilling operations, the drawworks 30 is operated to control the weight on bit, which is an important parameter that affects the rate of penetration. The operation of the drawworks is well known in the art and is thus not described in detail herein.

During drilling operations, a suitable drilling fluid 31 from a mud pit (source) 32 is circulated under pressure through a channel in the drillstring 20 by a mud pump 34. The drilling fluid passes from the mud pump 34 into the drillstring 20 via a desurger 36, fluid line 28 and Kelly joint 21. The drilling fluid 31 is discharged at the borehole bottom 51 through an opening in the drill bit 50. The drilling fluid 31 circulates uphole through the annular space 27 between the drillstring 20 and the borehole 26 and returns to the mud pit 32 via a return line 35. The drilling fluid acts to lubricate the drill bit 50 and to carry borehole cutting or chips away from the drill bit 50. A sensor $S_1$ preferably placed in the line 38 provides information about the fluid flow rate. A surface torque sensor $S_2$ and a sensor $S_3$ associated with the drillstring 20 respectively provide information about the torque and rotational speed of the drillstring. Additionally, a sensor (not shown) associated with line 29 is used to provide the hook load of the drillstring 20.

In one embodiment of the disclosure, the drill bit 50 is rotated by only rotating the drill pipe 22. In another embodiment of the disclosure, a downhole motor 55 (mud motor) is disposed in the drilling assembly 90 to rotate the drill bit 50 and the drill pipe 22 is rotated usually to supplement the rotational power, if required, and to effect changes in the drilling direction.

In the embodiment of FIG. 1, the mud motor 55 is coupled to the drill bit 50 via a drive shaft (not shown) disposed in a bearing assembly 57. The mud motor rotates the drill bit 50 when the drilling fluid 31 passes through the mud motor 55 under pressure. The bearing assembly 57 supports the radial and axial forces of the drill bit. A stabilizer 58 coupled to the bearing assembly 57 acts as a centralizer for the lowermost portion of the mud motor assembly.

In one embodiment of the disclosure, a drilling sensor module 59 is placed near the drill bit 50. The drilling sensor module contains sensors, circuitry and processing software and algorithms relating to the dynamic drilling parameters. Such parameters preferably include bit bounce, stick-slip of the drilling assembly, backward rotation, torque, shocks, borehole and annulus pressure, acceleration measurements and other measurements of the drill bit condition. A suitable telemetry or communication sub 72 using, for example, two-way telemetry, is also provided as illustrated in the drilling assembly 100. The drilling sensor module processes the sensor information and transmits it to the surface control unit 40 via the telemetry system 72.

The communication sub 72, a power unit 78 and an MWD tool 79 are all connected in tandem with the drillstring 20. Flex subs, for example, are used in connecting the MWD tool 79 in the drilling assembly 90. Such subs and tools form the bottom hole drilling assembly 90 between the drillstring 20 and the drill bit 50. The drilling assembly 90 makes various measurements including the pulsed nuclear magnetic resonance measurements while the borehole 26 is being drilled. The communication sub 72 obtains the signals and measurements and transfers the signals, using two-way telemetry, for example, to be processed on the surface. Alternatively, the signals can be processed using a downhole processor in the drilling assembly 90.

The surface control unit or processor 40 also receives signals from other downhole sensors and devices and signals from sensors $S_1$-$S_3$ and other sensors used in the system 10 and processes such signals according to programmed instructions provided to the surface control unit 40. The surface control unit 40 displays desired drilling parameters and other information on a display/monitor 42 utilized by an operator to control the drilling operations. The surface control unit 40 preferably includes a computer or a microprocessor-based processing system, memory for storing programs or models and data, a recorder for recording data, and other peripherals. The control unit 40 is preferably adapted to activate alarms 44 when certain unsafe or undesirable operating conditions occur. The system also includes a downhole processor, sensor assembly for making formation evaluation and an orientation sensor. These may be located at any suitable position on the bottomhole assembly (BHA).

Figure 2:
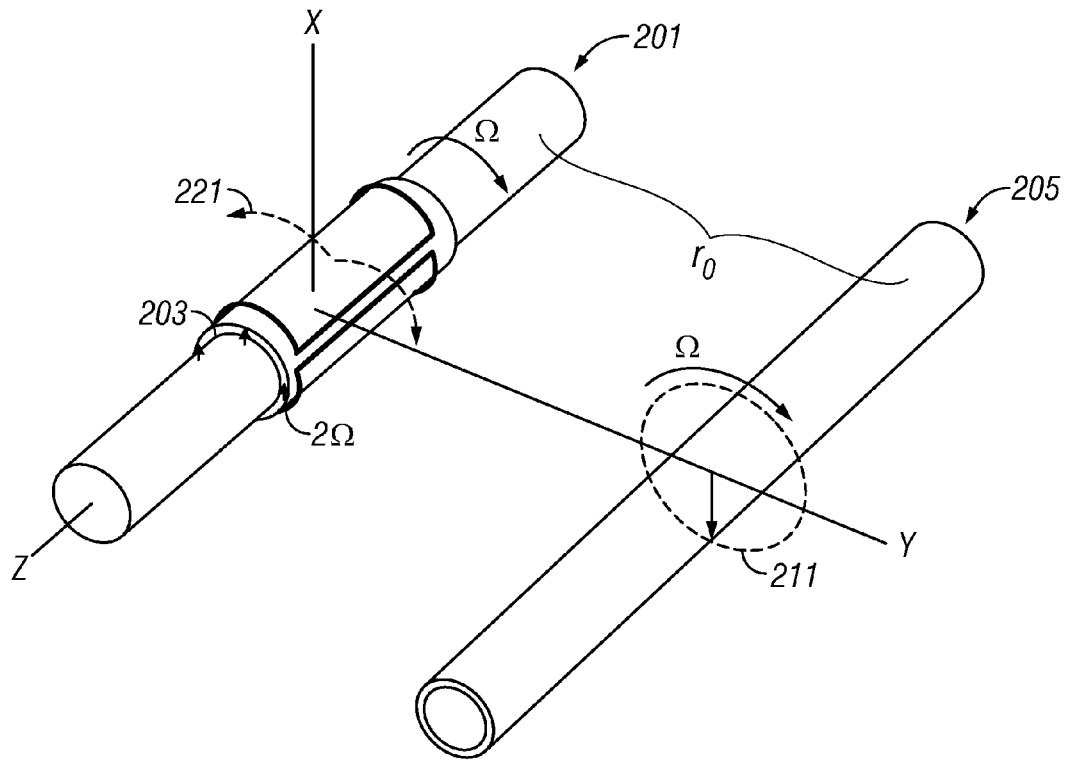
FIG. 2 shows a simplified layout of the magnetometer and the coordinate system used for the calculations.

Turning now to FIG. 2, a permanent magnet 203 is shown on a drill collar section 201 of the secondary well. The magnet is transversely magnetized with the flux direction indicated by 221. The pre-existing well casing is denoted by 205. The coordinate axes x, y, and z are as indicated in the figure. The collar section is provided with a coil 213. The coil rotates synchronously with the magnet, but the magnet-coil combination need not be synchronous with the rotation of the drill collar: this may be done by having the magnet-coil combination on a sleeve. The rotating magnet generates a variable magnetic field at a magnetic object such as the casing 205 of the pre-existing well. This variable magnetic field induces magnetization in the casing that, in turn, generate a variable magnetic flux picked up by the rotating coil 213.

The magnetic field generated by the magnet at the target well position can be approximated by the point dipole formula:

$$\vec{H}_{MAGNET} = \frac{1}{4\pi}\left[\frac{3(\vec{p}_m \cdot \vec{r})}{r^5} - \frac{\vec{p}_m}{r^3}\right], \quad (1)$$

Where $\vec{p}_m$ is the dipole moment of the magnet, and $\vec{r}$ is the distance from the magnet center to a point on the casing 205. When the magnet 203 rotates in the XY plane with angular velocity ω, then $$\vec{p}_m = p_m[\cos(\omega t)\vec{e}_x + \sin(\omega t)\vec{e}_y] \quad (2),$$

where $\vec{e}_x$ and $\vec{e}_y$ unit vectors in the x- and y-directions respectively. The rotating coil sensitivity function (magnetic field produced by the coil driven with a unit current) can be written as:

$$\vec{S}_{COIL} = \frac{A_{COIL}}{p_m} \cdot \vec{H}_{MAGNET}. \quad (3)$$

Here $\vec{S}_{COIL}$ is the sensitivity function of the coil and $A_{COIL}$ is the effective area of the coil.

The rotating magnet generates variable magnetization in the casing. The magnetization induces a variable magnetic flux in the coil. Based on the principle of reciprocity, the corresponding voltage can be expressed as:

$$V_{COIL} = \mu_0 \frac{d}{dt}\left[\int_{CASING\ VOLUME} \vec{M}_{CASING}(\vec{r}, t) \cdot \vec{S}_{COIL}(\vec{r}, t)\, dv\right], \quad (4)$$

where $\vec{M}_{CASING}$ is the magnetization of the casing, and $\vec{S}_{COIL}$ is the coil sensitivity function.

In eqn. (4) the sensitivity $\vec{S}_{COIL}$ can be considered as a slowly varying function over the cross-sectional area of the casing. Therefore, we can introduce a magnetization average over the cross-sectional area of the casing as:

$$\langle \vec{M}_{CASING} \rangle = \frac{1}{A_{CASING}} \cdot \int_{CROSS\_SECTION} \vec{M}_{CASING}(\vec{r}, t)\, ds \approx \quad (5)$$

$$\chi_{eff\_xy} \cdot \vec{H}_{MAGNET\_XY}(\vec{r}_a, t) + \chi_{eff\_z} \cdot \vec{H}_{MAGNET\_Z}(\vec{r}_a, t),$$

Where $\chi_{eff\_xy}$ and $\chi_{eff\_z}$ are the effective magnetic susceptibilities in the direction perpendicular and parallel to the casing axis respectively, $A_{CASING}$ is the effective area of the casing, and $\vec{r}_a$ represents points along the axis of the casing. Due to the shape of the casing we can use the following simlification: $\chi_{eff\_xy} \ll \chi_{eff\_z}$ This then gives, for the coil voltage, the equation:

$$V_{COIL} = \mu_0 \cdot \chi_{eff\_z} \cdot A_{CASING} \cdot \frac{A_{COIL}}{p_m} \cdot \frac{d}{dt} \quad (6)$$

$$\left(\int_{CASING\_LENGTH} |H_{MAGNET\_Z}(\vec{r}_a, t)|^2\, dr_a\right).$$

This then gives the approximate result $$V_{COIL} = \frac{3\mu_0 \cdot \chi_{eff\_z} \cdot A_{CASING} \cdot A_{COIL} \cdot p_m \cdot \omega}{64\pi^2 \cdot r_0^5} \cdot \cos(2\omega \cdot t). \quad (7)$$

Here $A_{CASING}$ is the cross-sectional area of the casing.

For practical values $\chi_{eff\_z}=100$, $A_{CASING}=2\pi \cdot 10^{-3}$ m$^2$, $\omega=2\pi$ 5 s$^{-1}$, $A_{COIL}=0.2\cdot 200$ m$^2$, $p_m=1000$ A·m$^2$, and separation between wells $r_0=10$ m, the estimated voltage amplitude $V_m=48$ nV. In case the thermal noise in the coil and the preamplifier noise are the only sources of noise the signal-to-noise ratio per 1 second measurement time can be expected to be around 20. If $r_0=5$ m, then $V_m=0.75$ µV.

It is important to note from eqn. (7) that the voltage induced in the rotating coil by the rotating magnetization of the casing has a frequency which is twice the rotation frequency of the magnet/coil assembly. This means that the measured proximity signal is relatively easy to separate from a parasitic signal induced in the rotating coil due to the earth's magnetic field. The parasitic signal has a frequency equal to the magnet/coil rotation frequency.

The main sources of error in the measurement technique is due to the presence of some second harmonic in the magnet/coil assembly rotation. In this case the earth's magnetic field related signal would appear at the frequency $2\omega$ thus giving a spurious signal at the same frequency as the expected proximity signal. Fortunately, the presence of $2\omega$-component in the rotation speed can be assessed with an accelerometer and then the data can be used for eliminating the spurious signal from the measurement results. The second harmonic signal is easy to calculate from the accelerometer output, known value and direction of the earth's magnetic field, and measurements of borehole inclination and azimuth. A gyro survey may be needed to get the borehole inclination and azimuth.

Figure 3:
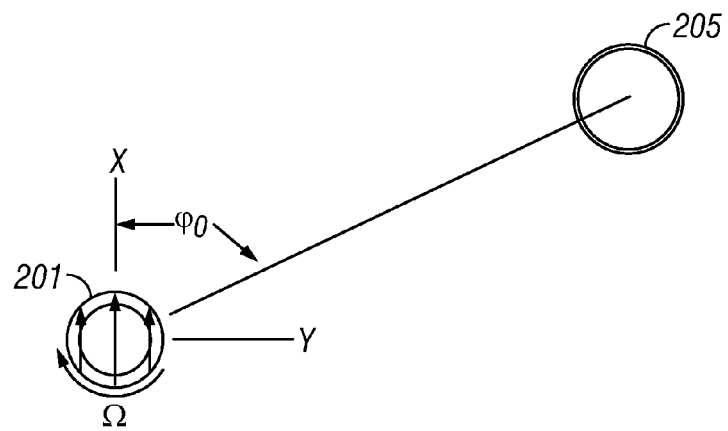
FIG. 3 illustrates azimuthal dependence of the signal in the sensor coil.

FIG. 3 illustrates azimuthal dependence of the voltage on the rotating coil 213. Using reference voltage $$V_{REF} \propto \cos(2\omega \cdot t), \quad (8)$$

synchronized with the magnet/coil rotation, the following expression for the voltage on the coil 213 can be written $$V_{REF} = V_m \cdot \cos[2(\omega \cdot t + \phi_0)]. \quad (9)$$

Here $\phi_0$ is the azimuth of the casing with respect to the secondary well. Thus the phase of the signal on the coil 213 is sensitive to the azimuthal position of the casing 205 with respect to the secondary well 201.

Figure 4:
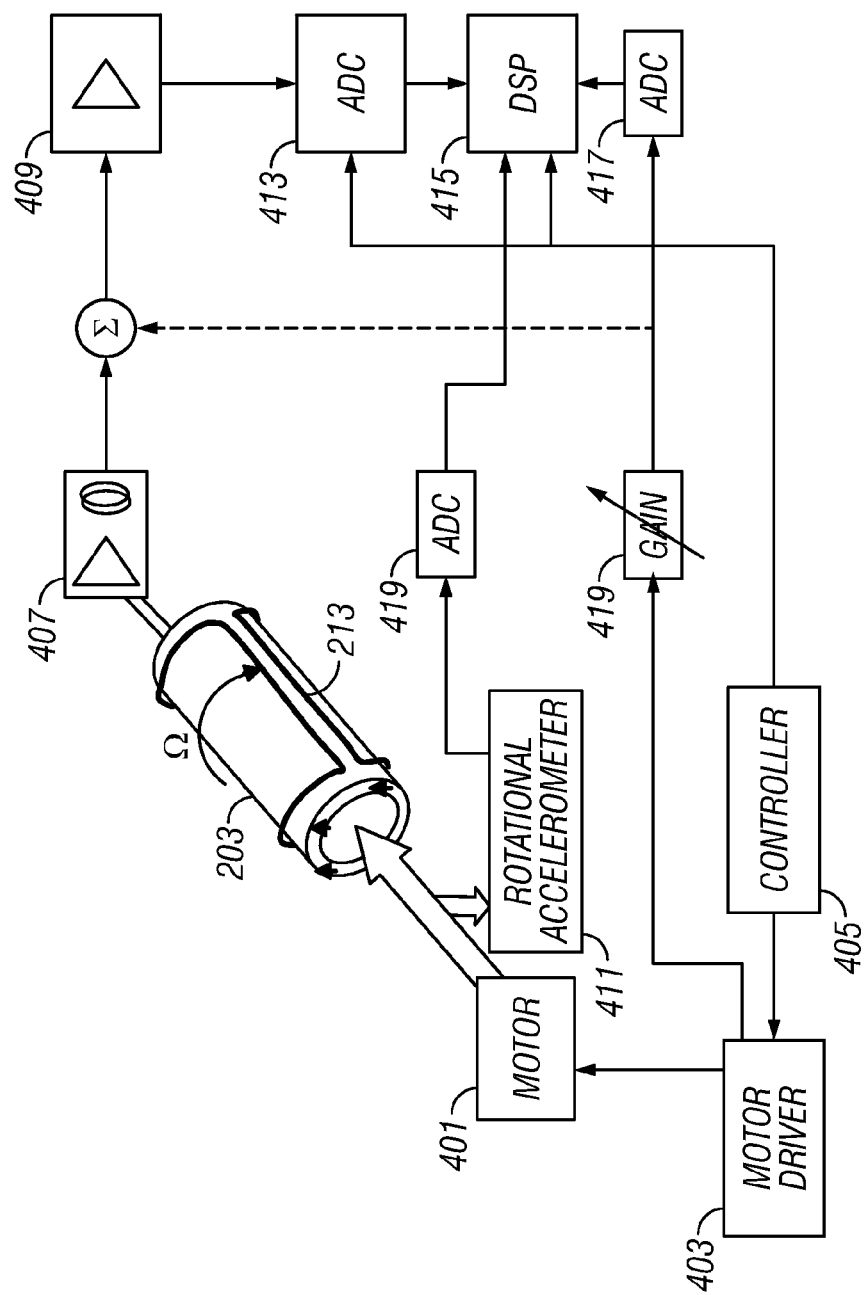
FIG. 4 is a schematic illustration of implementation of the rotational magnetometer.

FIG. 4 is a block diagram illustrating an implementation of the rotational magnetometer. The magnetometer comprises a motor 401 rotating the magnet 203 and the coil 213. The signal from the coil 213 transferred to the low noise preamplifier 409 via an adapter (e.g. sliding rings) 407. Provision is made to eliminate parasitic signal $2\omega$ generated by the Earth's magnetic field in presence of rotational disturbances: the signals from rotational accelerometer 411 and the motor driver 403 are used to eliminate parasitic signals from the measurement data. Serving this purpose are also a controller 405, analog-to-digital converters 413, 417, 419, digital signal processor 415 and a variable gain amplifier 419.

Those versed in the art and having benefit of the present disclosure would recognize that it is sufficient for the coil 213 to be able to be responsive to a component of the magnetic flux due to the induced magnetization that is transverse to the z-axis. The configuration of the coil 213 shown in FIG. 2 is not the only arrangement that would provide a suitable signal, but it is one of the better designs. In principle, an inclined planar coil on the BHA with the coil axis inclined to the z-axis would work. For a coil placed on the magnet 201 the signal would be greatest when the coil axis is transverse to the z-axis. Similarly, the magnet does not have to be a transversally magnetized cylindrical magnet as indicated by 201. The method would also work, albeit less efficiently, using a bar magnet with its magnetization direction having a component parallel to the z-axis. Those versed in the art and having benefit of the present disclosure would recognize also that a longitudinal coil spaced axially apart from the magnet 201 can be used to receive proximity signal originating from variable Z-component of the magnetization of the casing.

Figure 5:
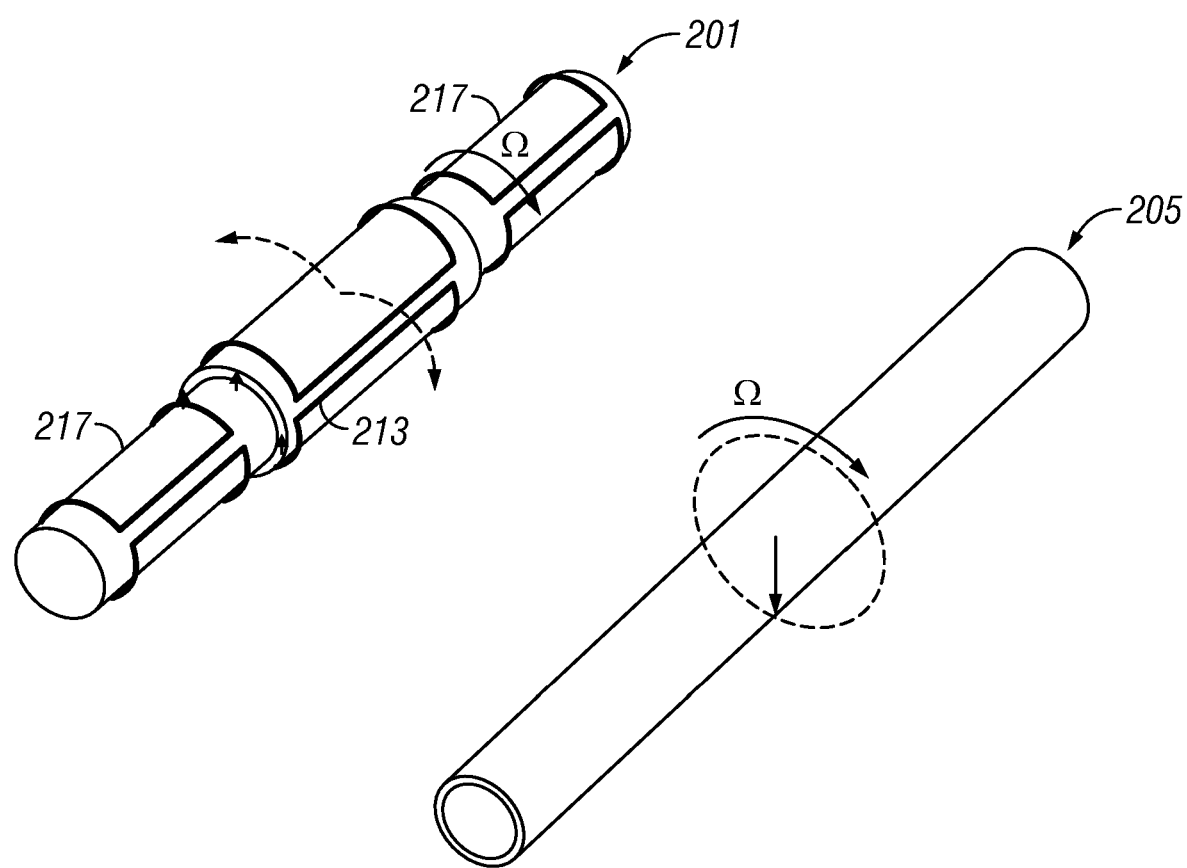
FIG. 5 shows an embodiment that utilizes a pair of additional differentially connected coils synchronously rotating with the magnetic coil.

FIG. 5 illustrates an example of embodiment of the technique that utilizes a pair of additional differentially connected coils 217 synchronously rotating with the magnet/coil assembly. The additional coil assembly is sensitive to non-parallel orientation of the wells, i.e., the output will be zero if the two boreholes are parallel. Any differential pair of identical coils placed asymmetrically with respect to the magnet will also be sensitive to the DC magnetization of the casing (gives additional proximity information) and not sensitive to the Earth's magnetic field. This is particularly useful when it is desired to drill the secondary well to intersect the pre-existing well.

An important feature of the rotational magnetometer described above is that the source of the magnetic field producing variable magnetization in the magnetic casing does not induce any direct signal in the synchronously rotating coil 213. This makes the induction method with the source and the sensor coil placed in one well feasible. Another way to eliminate the direct field signal is to use transient mode of inducing magnetization in the target casing—transient magnetometer.

Figure 6:
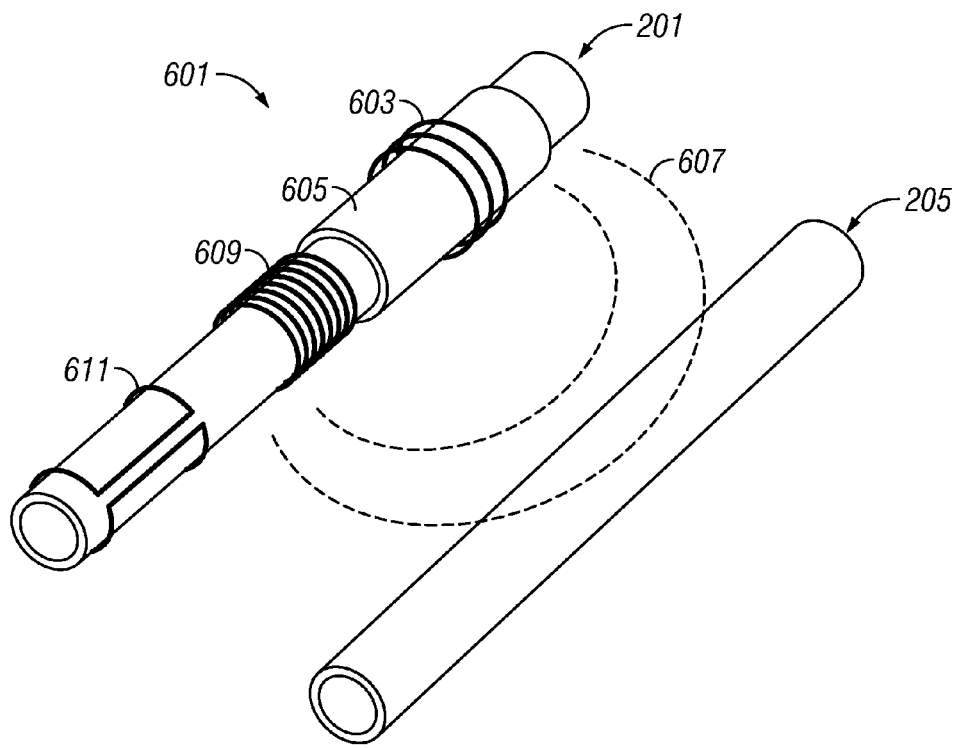
FIG. 6 Shows an embodiment that utilizes switchable magnetic field source.

FIG. 6 depicts an embodiment of the transient magnetometer. The magnetometer comprises a source of switchable magnetic field 601 having a switching coil 603 and a magnetic core 605. The magnetic field source 601 generates magnetic field (the isolines of the field are shown at 607) at a position of the target casing 205. The magnetic core 605 preferably comprises a magnetic material with residual magnetization. The residual magnetization is used to provide a strong magnetic dipole without the need for a DC current driving the switching coil and causing a significant energy loss if a strong magnetic field needs to be generated (the application of the magnetic material with residual magnetization in a source of a strong switchable magnetic field is described in U.S. patent application Ser. No. 11/037,488). Disclosed therein is a magnetic core having residual magnetization. Switching the current in the coil results in magnetization reversal in the magnetic core and change in magnetic dipole moment. After the magnetization reversal is complete the current is removed and the new vector of magnetic dipole of the maintains constant (steady-state phase of the antenna dipole) due to magnetic hysteresis of magnetic material employed for the magnetic core. The magnetometer also comprises a longitudinal coil 609 to pickup a variable magnetic flux produced by the casing magnetization transient occurring in response to switching of the magnetization in the magnetic core 605. The magnetometer further comprises a transversal coil 611, the signal induced in this coil is sensitive to the azimuthal position of the casing with respect to the secondary well 201 when the drill collar rotates.

Figure 7:
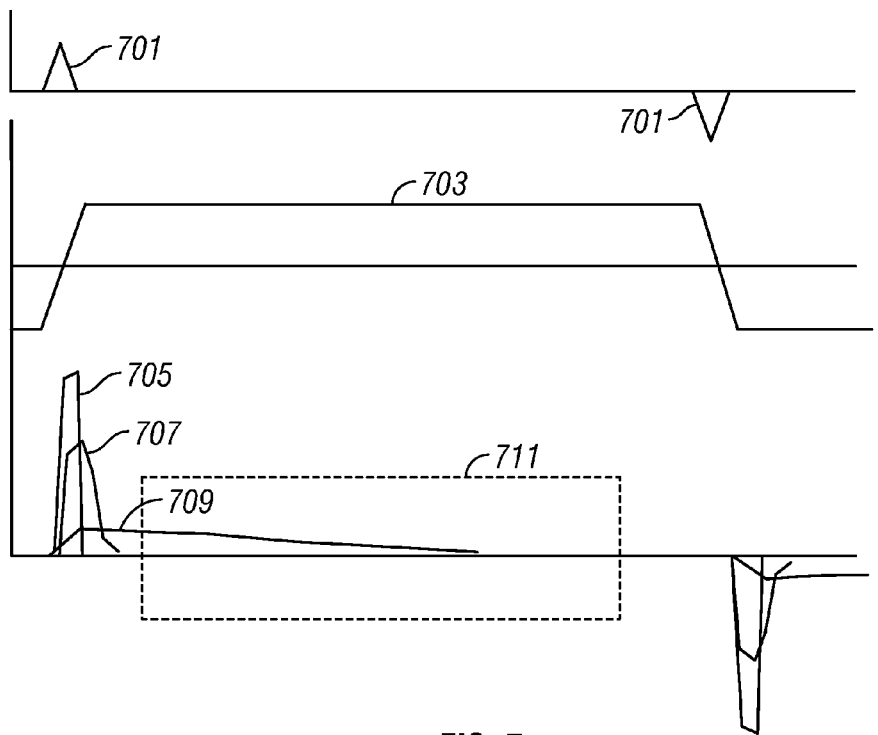
FIG. 7 shows time diagrams of the switchable magnetic field and the transient responses (corresponds to the embodiment of FIG. 6)

FIG. 7 shows time diagrams of the switchable magnetic field and the transient responses in the coil 609. The switchable magnetic field 703 is generated by switching polarity of the residual magnetization in the magnetic core 605. The switching polarity is accomplished by driving the switching coil 603 with short pulses of electric current 701. Decaying signals 705, 707, 709 (transients) in the coil 609 are generated in response to a fast switching off or changing polarity of a "static" magnetic field. The signals are associated with direct coupling between the source and the sensing coil (transient at 705), the signal due to eddy currents in the surrounding rock formations and the conductive collar of the drill string (a conductive body) placed in the well 201 (transient at 707), and casing proximity signal due to variable magnetization of the magnetic casing 205 (transient at 709). It is important for the method that the proximity signal 709 is substantially longer than the undesired signals 705 and 707. It follows from the fact that a time constant of the transient decay is proportional to the effective magnetic permeability of a magnetic conductor. It is to be noted that unlike in the first embodiment, the direction of the magnetic field does not rotate—it only switches polarity. As the coil 609 is also longitudinal, no sinusoidal variation will occur.

The following expression for the time constant of building up of the average (over the cross-sectional area) magnetization of the casing can be used [see, for example, Polivanov, K. M. Electrodinamika veshchestvennykh sred, 1988]

$$\tau \propto \delta^2 \cdot \mu_0 \cdot \mu \cdot \sigma. \tag{10}$$

Here $\delta$ is the wall thickness of the casing, $\mu$ is the magnetic permeability, which is about 100 for a typical casing material, and $\sigma$ is the conductivity of the material of the casing. The process of buiding up of the magnetic flux in the coil 609 is exponential with the time constant given by eqn. (10). By the time approximately equal to the time constant of the casing magnetization process all other transients will substantially decay. Thus, by measuring the signal in a time window (at 711) starting after a time comparable with the time constant of building up of the casing magnetization (time window 711) one effectively eliminates all undesired signal. The expected time constant of the direct coupling is of the order of the duration of the pulses 701. In one embodiment, the area within the window is used as a distance indicator. Appropriate calibration is carried out. The processes due to the eddy current in the conductive surroundings are in the range 1-100 µs. The signal from the magnetic casing should last approximately 10-30 ms. Thus practical acquisition window may be positioned between 1 ms and 50 ms. Those versed in the art and having benefit of the present disclosure would recognize that it is sufficient that the magnet has a longitudinal component, and the coil is oriented so that is responsive to magnetic flux changes in the longitudinal direction.

Figure 8:
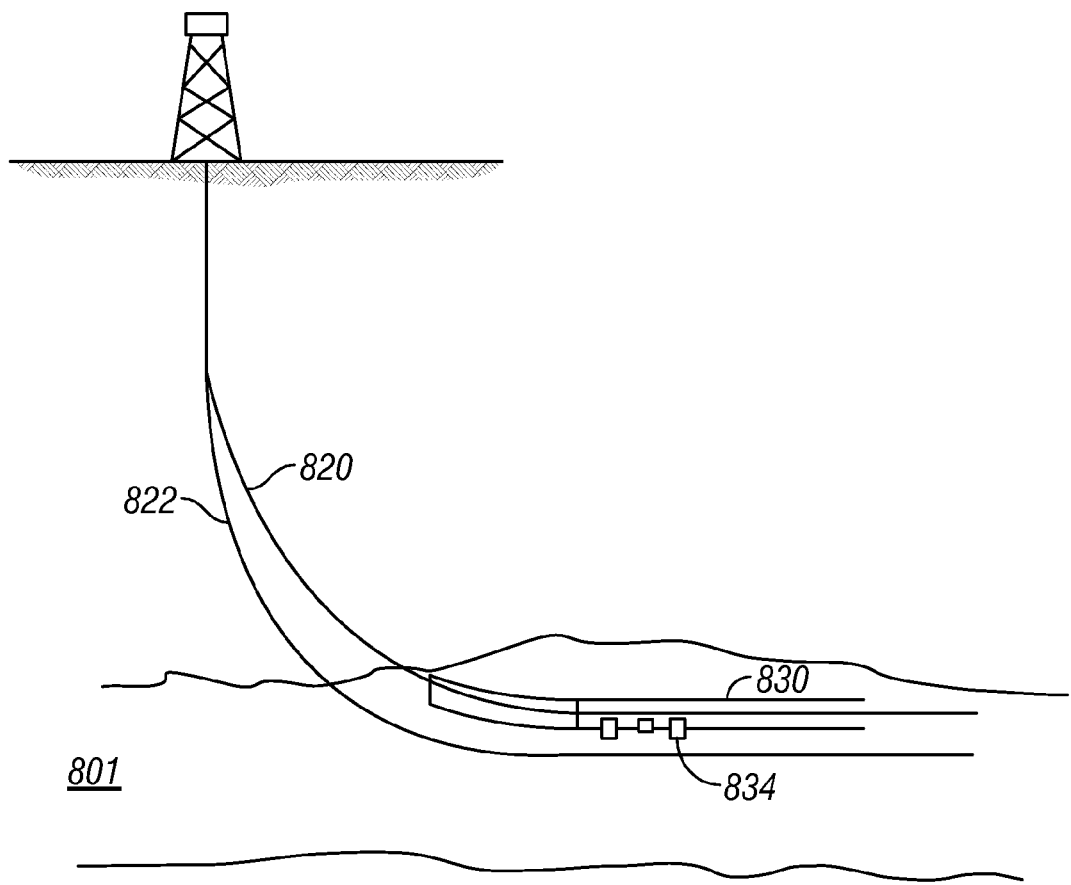
FIG. 8 shows drilling a second borehole in accurate and close proximity to a cased production borehole.

FIG. 8 illustrates an embodiment of the invention in secondary recovery operations. A producing wellbore 820 has been drilled into a reservoir interval 801 that contains hydrocarbons. For various reasons, such as low formation pressure or high viscosity of the hydrocarbons in the reservoir, production under natural conditions of hydrocarbons may be at uneconomically low rates. In such cases, a second wellbore 822 is drilled, typically as a sidebore from the wellbore 820 so as to be substantially parallel to the main wellbore within the reservoir. The producing wellbore is typically cased with casing 830 that has perforations 834. Fluid, such as water, $CO_2$ or steam is then injected into the formation through the secondary wellbore 822 and the injected fluid drives the hydrocarbons in the formation towards the producing wellbore 820 where it may be recovered. Such an operation requires careful positioning of the secondary borehole 822 in proximity to the production wellbore 820. This may be done by monitoring the voltage in the coil. As can be seen from eqn. (7), the voltage varies inversely as the fifth power of the distance. Thus, the voltage measurements may be used as either relative distance indicators based on voltage changes, or, with proper calibration, as absolute distance indicators.

The processing of the data may be done by a downhole processor to give corrected measurements substantially in real time. Implicit in the control and processing of the data is the use of a computer program on a suitable machine readable medium that enables the processor to perform the control and processing. The machine readable medium may include ROMs, EPROMs, EEPROMs, Flash Memories and Optical disks.

While the foregoing disclosure is directed to the preferred embodiments of the disclosure, various modifications will be apparent to those skilled in the art. It is intended that all variations within the scope and spirit of the appended claims be embraced by the foregoing disclosure.

What is claimed is:

1. A method of determining a distance to a first borehole from a second borehole, the method comprising:
   producing a time varying magnetic field in the first borehole by rotating a magnet in the second borehole at a first rotational speed and inducing a magnetization in a magnetic object in the first borehole;
   rotating a coil in the second borehole synchronously with the magnet for producing a signal responsive to a magnetic flux resulting from the magnetization;
   removing a component of the signal, wherein the component is at twice the rotational speed and due to earth's magnetic field; and
   estimating the distance using a remainder of the signal at twice the rotational speed.

2. The method of claim 1 wherein the magnetic object in the first borehole comprises a casing.

3. The method of claim 1 further comprising using the estimated distance to generate the second borehole in a desired relation to the first borehole that is selected from: (i) substantially parallel, and (ii) intersecting.

4. The method of claim 1 further comprising conveying the magnet on a bottomhole assembly on a drilling tubular into the second borehole.

5. The method of claim 1 further comprising:
   (i) measuring the first rotational speed, and
   (ii) determining the component at twice the rotational speed and due to the earth's magnetic field.

6. The method of claim 1 further comprising:
   (i) measuring an additional signal using a pair of differentially connected coils responsive to the magnetic flux, and
   (ii) using the additional signal as an indicator of an inclination between an axis of the first borehole and an axis of the second borehole.

7. The method of claim 1 wherein the first rotational speed is substantially the same as a rotational speed of a bottomhole assembly.

8. A method of determining a distance to a first borehole from a second borehole, the method comprising:
   producing transient magnetic field in the first borehole by switching a polarity of a magnet having a substantially longitudinal magnetization in the second borehole and inducing a transient magnetization of a magnetic object in the first borehole,
   using a coil in the second borehole for producing a signal responsive to a magnetic flux resulting from the induced magnetization; and
   estimating the distance using a portion of the signal substantially excluding a component due to eddy currents in a formation and eddy currents in a conductive body in the second borehole.

9. The method of claim 8 wherein estimating the distance further comprises using a portion of the signal substantially excluding a component of the signal due to a direct coupling of the magnet and the coil.

10. The method of claim 8 further comprising using a transverse coil for producing a signal indicative of an orientation of the second borehole relative to the first borehole, the transverse coil being substantially transverse to a longitudinal axis of the second borehole.

11. The method of claim 8 wherein estimating the distance further comprises using a windowed portion of the signal.

12. An apparatus configured to determine a distance to a first borehole from a second borehole, the apparatus comprising:
(a) a magnet configured to be conveyed in the second borehole, rotate at a first rotational speed, produce a time varying magnetic field in the first borehole and induce a magnetization in a magnetic object in the first borehole;
(b) a coil in the second borehole configured to rotate synchronously with the magnet and produce a signal responsive to a magnetic flux resulting from the magnetization; and
(c) a processor configured to:
removing a component of the signal, wherein the component is at twice the rotational speed and due to earth's magnetic field, and
estimate the distance using a remainder of the signal at twice the rotational speed.

13. The apparatus of claim 12 wherein the magnetic object in the first borehole comprises a casing.

14. The apparatus of claim 12 wherein the processor is further configured to use the estimated distance to generate the second borehole in a desired relation to a path of the first borehole that is selected from: (i) substantially parallel, and (ii) intersecting.

15. The apparatus of claim 12 further comprising a bottomhole assembly on a drilling tubular configured to convey the magnet into the second borehole.

16. The apparatus of claim 12 further comprising an accelerometer configured to measure the first rotational speed; and wherein the processor is further configured to:
determine the component at twice the rotational speed and due to the earth's magnetic field.

17. The apparatus of claim 12 further comprising a pair of differentially connected coils responsive to the magnetic flux configured to produce an additional signal, and
wherein the processor is further configured to use the additional signal as an indicator of an inclination between an axis of the first borehole and an axis of the second borehole.

18. The apparatus of claim 12 wherein the first rotational speed is substantially the same as a rotational speed of a bottomhole assembly.

19. The apparatus of claim 12 further comprising a transverse coil configured to produce a signal indicative of an orientation of the second borehole relative to the first borehole, the transverse coil being substantially transverse to a longitudinal axis of the apparatus.

20. An apparatus configured to determine a distance from a first borehole to a second borehole, the apparatus comprising:
(i) a switchable magnet having a substantially longitudinal magnetization in the second borehole configured to produce a transient field in the first borehole and induce a transient magnetization in a magnetic object in the first borehole;
(ii) a coil in the second borehole configured to produce a signal responsive to a magnetic flux resulting from the magnetization; and
(iii) a processor configured to estimate the distance using a portion of the signal substantially excluding a component due to eddy currents in a formation and eddy currents in a conductive body in the second borehole.

21. The apparatus of claim 20 wherein the processor is further configured to estimate the distance using a portion of the signal substantially excluding a component of the signal due to a direct coupling of the magnet and the coil.

22. The apparatus of claim 20 wherein the magnetic object in the first borehole comprises a casing.

23. The apparatus of claim 20 further comprising a bottomhole assembly on a drilling tubular configured to convey the magnet into the second borehole.

24. A non-transitory computer-readable medium product having stored thereon instructions that when read by at least one processor cause the at least one processor to perform a method, the method comprising:
producing a time varying magnetic field in a first borehole by rotating a magnet in a second borehole at a first rotational speed and inducing a magnetization in a magnetic object in the first borehole;
rotating a coil in the second borehole synchronously with the magnet for producing a signal responsive to a magnetic flux resulting from the magnetization;
removing a component of the signal, wherein the component is at twice the rotational speed and due to earth's magnetic field; and
estimating the distance using a remainder of the signal at twice the rotational speed.

* * * * *